United States Patent [19]

Du Bae

[11] 4,292,673
[45] Sep. 29, 1981

[54] VISCOSIMETER

[75] Inventor: Hyung Du Bae, Brea, Calif.

[73] Assignee: International Telephone and Telegraph Corporation, New York, N.Y.

[21] Appl. No.: 128,666

[22] Filed: Mar. 10, 1980

[51] Int. Cl.³ .......................................... G01N 11/02
[52] U.S. Cl. ...................................... 364/509; 73/54; 364/558
[58] Field of Search ...................... 364/509, 510, 558; 73/32 R, 32 A, 54, 194 B, 194 M, 570

[56] References Cited

U.S. PATENT DOCUMENTS

| | | | |
|---|---|---|---|
| 3,710,614 | 1/1973 | Oppliger | 73/54 |
| 3,878,374 | 4/1975 | Schlatter | 364/558 |
| 3,903,731 | 9/1975 | Sieben | 73/54 |
| 4,020,330 | 4/1977 | Bae | 364/558 |
| 4,023,400 | 5/1977 | November | 73/54 |
| 4,154,093 | 5/1979 | Smith et al. | 73/54 |
| 4,184,364 | 1/1980 | Du Bae | 73/54 |

OTHER PUBLICATIONS

Ashwin et al., "Viscometers Having Damped Torsional Oscillation," *Jnl. of Sci. Instr.*, vol. 37, Dec. 1960, pp. 480–485.

*Primary Examiner*—Errol A. Krass
*Attorney, Agent, or Firm*—A. Donald Stolzy

[57] ABSTRACT

A vibration viscosimeter having a resilient wire loop to be vibrated and an electrical drive therefor. The energizing signal for the drive is alternately kept 30 degrees lagging and 30 degrees leading the vibration or vice versa. Viscosity may then be computed as a function of the signal periods and six constants.

4 Claims, 8 Drawing Figures

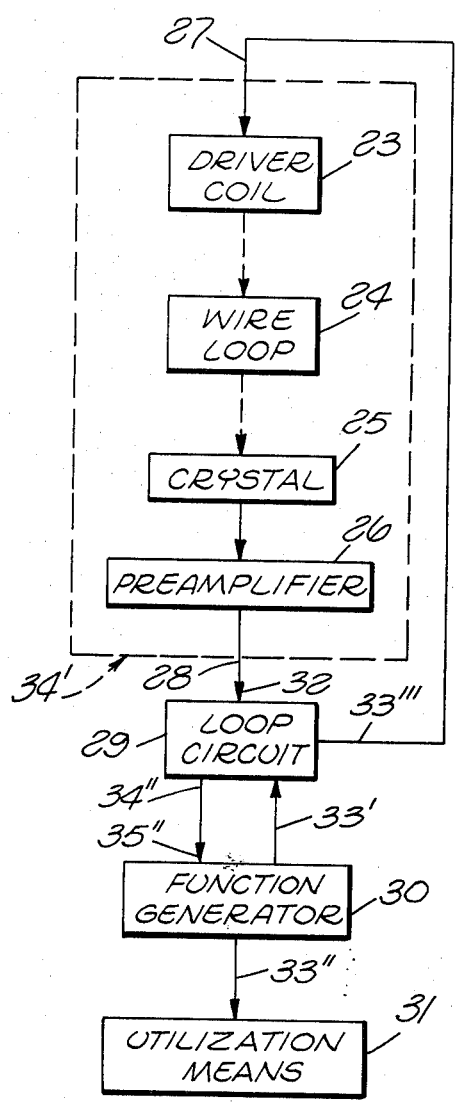
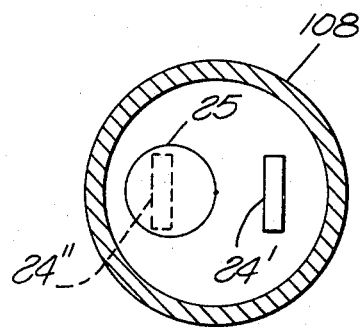
FIG. 7
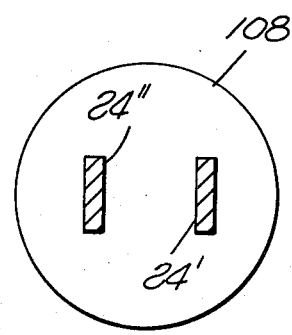
FIG. 8
FIG. 1

0

VISCOSIMETER

BACKGROUND OF THE INVENTION

This invention relates to vibration instruments, and more particularly to a vibration viscosimeter.

PRIOR ART STATEMENT

Some of the structure disclosed herein is or may be identical to that disclosed in M. H. November, U.S. Pat. No. 4,283,936, issued Aug. 18, 1981, and that disclosed in G. L. Schlatter U.S. Pat. No. 4,037,459 issued July 26, 1977.

See also C. E. Miller et al U.S. Pat. No. 3,677,067 issued July 18, 1972; C. E. Miller U.S. Pat. No. 3,741,000 issued June 26, 1973; M. H. November et al U.S. Pat. No. 4,037,460 issued June 26, 1973; M. H. November, U.S. Pat. No. 4,194,385 issued Mar. 25, 1980; G. L. Schlatter U.S. Pat. No. 3,878,374 issued Apr. 15, 1975, and G. L. Schlatter U.S. Pat. No. 3,769,831 issued Nov. 6, 1973.

SUMMARY OF THE INVENTION

In accordance with the viscosimeter of the present invention, a body is vibrated. Viscosity is then calculated from certain periods of the vibrations.

BRIEF DESCRIPTION OF THE DRAWINGS

In the accompanying drawings which illustrate exemplary embodiments of the present invention:

FIG. 1 is a block diagram of a viscosimeter constructed in accordance with the present invention;

FIGS. 7 and 8 are transverse sectional view taken on the lines 7—7 and 8—8, respectively, shown in FIG. 6.

DESCRIPTION OF THE PREFERRED EMBODIMENTS

Figure 2:
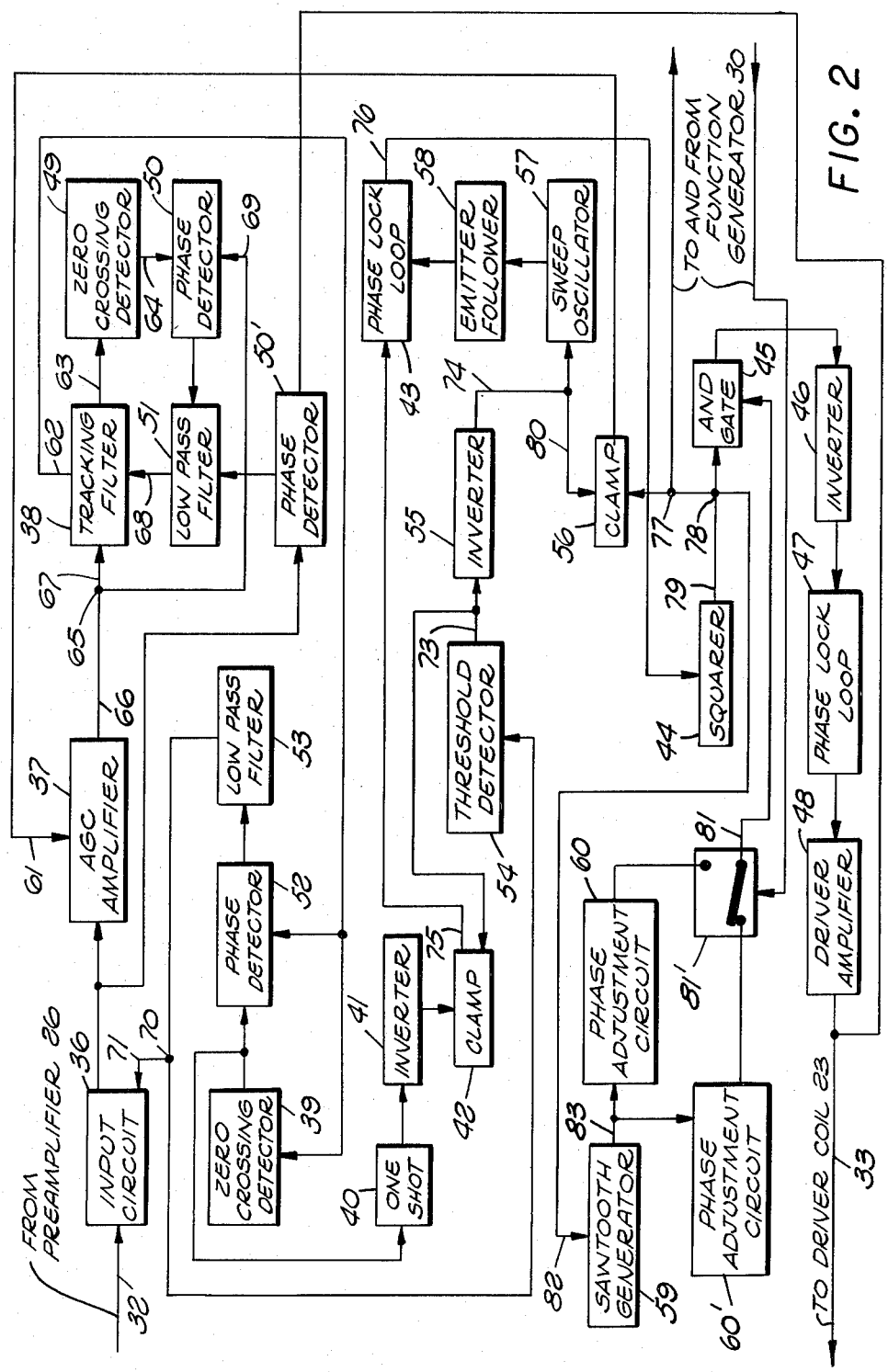
FIG. 2 is a diagrammatic view of a loop circuit shown in FIG. 1.

In the drawings, in FIG. 1, a vibration viscosimeter probe is indicated at 34' having a driver coil 23, a vibratable resilient wire loop 24, a piezoelectric crystal 25 and a preamplifier 26.

Probe 34' has an input lead 27 and an output lead 28.

Other blocks shown in FIG. 1 are a loop circuit 29, a function generator 30 and utilization means 31. Loop circuit 29 has an input lead 32 and output leads 33''' and 34''. Function generator 30 has input leads 35'' and 33' connected to and from function generator 30. The output leads 33' and 33'' of function generator 30 are connected to loop circuit 29 and utilization means 31, respectively.

The output lead 28 of probe 34' is connected to the input lead 32 of loop circuit 29. The input lead 27 of probe 34' is connected from the output lead 33''' of loop circuit 29. Probe 34' and loop circuit 29 form a closed loop electromechanical oscillator. Wire loop 24 is submerged in a fluid. The density of the fluid is, at times, a function of the period at which wire loop 24 vibrates.

Function generator 30 may have its input lead 35 connected from lead 33''' or at other points in loop circuit 29. Loop circuit 29 impresses a square wave voltage on input lead 35 of function generator 30.

Utilization means 31 shown in FIG. 1 may be a viscosity indicator, a process controller or otherwise.

Probe 34', function generator 30 and utilization means 31 may be similar to those disclosed in U.S. Pat. No. 3,878,374. The same is true of everything shown in FIG. 2.

Probe 34' shown in FIG. 1 may be conventional except as described herein.

Preamplifier 26 shown in FIG. 1 may be conventional.

Loop circuit 29 is shown in FIG. 2 including an input circuit 36, an AGC amplifier 37, a tracking filter 38, a zero crossing detector 39, a one-shot multivibrator 40, an inverter 41, a clamp 42, a phase lock loop 43, a squarer 44, an AND gate 45, an inverter 46, a phase lock loop 47 and a driver amplifier 48 connected in succession as serial stages from input lead 32 of loop circuit 29 to its output lead 33''' and connected respectively from the output lead 28 of probe 34' to the input lead 27 of probe 34'.

In FIG. 2, other stages are a zero crossing detector 49, a phase detector 50, a low pass filter 51, a phase detector 52, a low pass filter 53, a threshold detector 54, an inverter 55, a clamp 56, a sweep oscillator 57, an emitter-follower 58, a saw-tooth generator 59 and two phase adjustment circuits 60 and 60' (manually adjustable only).

AGC amplifier 37 has an AGC input lead 61 connected from the output of clamp 56.

Tracking filter 38 has two output lead 62 and 63. Tracking filter output lead 63 is connected to the input of zero crossing detector 49. The output of zero crossing detector 49 is connected to one input 64 of phase detector 50. A junction is provided at 65 from which an output lead 66 of AGC amplifier 37 is connected. Tracking filter 38 has two input leads 67 and 68. Tracking filter input lead 67 is connected from junction 65. Lead 68 is connected from the output of low pass filter 51.

Phase detector 50 has a second input lead 69 connected from junction 65. The output of phase detector 50 is connected to one input of low pass filter 51. Phase detector 50' has one input connected from the output of input circuit 36 and another input connected from lead 33. Phase detector 50' has an output connected to another input of low pass filter 51.

The purpose of zero crossing detector 49, phase detector 50 and low pass filter 51 is to cause tracking filter 38 to track the frequency of output signal of AGC amplifier 37. Phase detector 50' causes the output driver amplifier 48 to track the phase (have a constant phase sum or difference relative to that) of the output signal of input circuit 36. The signal on the tracking filter 38, thus, causes the passband thereof to straddle the frequency of the input to tracking filter 38 over input lead 67, and to track the phase thereof as well.

The output of tracking filter 38 on output lead 62 thereof is 90 degrees out of phase with the signal on the output lead 63 thereof. The signal from the tracking filter output lead 62 is impressed upon zero crossing detector 39 and phase detector 52. The output of zero crossing detector 39 is impressed both upon phase detector 52 and one-shot 40. The output of phase detector 52 is impressed upon low pass filter 53.

A junction is provided at 70 connected from the output of low pass filter 53. A lead 71 is connected from junction 70 to input circuit 36 to the AGC input of an amplifier therein for automatic gain control.

Threshold detector 54 has an input connected from junction 70. This input of threshold detector 54, when below a predetermined potential, causes the potential of the output lead 73 of threshold detector 54 to go either high or low. The output lead 73 of threshold detector 54 is, thus, for example, either ground or +15 volts or +V1. When the output of low pass filter 53 is below the predetermined potential, output lead 73 of threshold detector 54 is at ground.

Threshold detector 54 operates both of the clamps 42 and 56 and the sweep oscillator 57. Clamp 56 and sweep oscillator 57 are operated through the inverter 55.

Inverter 55 has an output lead 74 which also assumes potentials of V1 or ground.

Clamp 42 either passes the output of inverter 41 to the phase lock loop 43 or in the other state of the threshold detector 54, clamp 42 having an output lead 75, is operated to clamp the output lead 75 to ground. The output of inverter 55 is simply the inverse of the output of threshold detector 54. When the output of inverter 55 is high, sweep oscillator 57 receives power. When the output of inverter 55 is low, the output of sweep oscillator 57 is at ground.

Emitter follower 58 is connected between sweep oscillator 57 and phase lock loop 43. Phase lock loop 43 has an output lead 76 which is connected to squarer 44. Junctions are provided at 77 and 78. Squarer 44 has an output lead 79 connected to junction 78. Junction 78 is connected to junction 77. Clamp 56 is connected from junction 77 to AGC amplifier input lead 61.

When the output of threshold detector 54 is high, loop circuit 29 is tracking and opens clamp 42 to unground the output lead 75 thereof. Conversely, at the same time, inverter 55 grounds the input to sweep oscillator 57 and disables it. During tracking, inverter 55 also disables the output of clamp 56 by a connection 80 from inverter output lead 74 to clamp 56.

During searching, threshold detector 54 holds the output of clamp 42 at ground while inverter 55 operates sweep oscillator 57 and clamp 56 passes the output of squarer 44 to the AGC input lead 61 of AGC amplifier 37.

In FIG. 2, junction 77 is connected to function generator 30 shown in FIG. 1.

AND gate 45 receives an input from junction 78 and from an output lead 81 of a switch 81' to provide alternately outputs from phase adjustment circuits 60 and 60'. Circuits 60 and 60' are manually set so that the voltage on lead 33 leads and lags the voltage on lead 32, respectively by plus (+)30 electrical degrees and minus (−)30 electrical degrees.

Sawtooth generator 59 has an input lead 82 connected from junction 78, and an output lead 83 connected to the inputs of phase adjustment circuits 60 and 60'.

Circuits 60 and 60' are manually adjustable to adjust the sine wave component of the output voltage of driver amplifier 48 through the use of certain structures including the phase adjustment circuits 60 and 60', themselves, and phase lock loop 47.

OPERATION

In the embodiment of the invention shown in FIG. 1, probe 34' and loop circuit 29 provide an electromechanical oscillator which oscillates at a frequency dependent upon the viscosity of the fluid in which wire loop 24 is immersed. The same is true of the pulse repetition frequency of the square wave voltage applied to the input lead 35" of function generator 30.

Function generator 30 may be described as a linearization circuit. It produces an output directly proportional to viscosity from the input signal thereto.

Except as noted hereinabove, the structures of FIGS. 1 and 2 may be identical to and operate in a manner similar to the manner in which the vibration densitometer of U.S. Pat. No. 4,037,459 operates.

Figure 3:
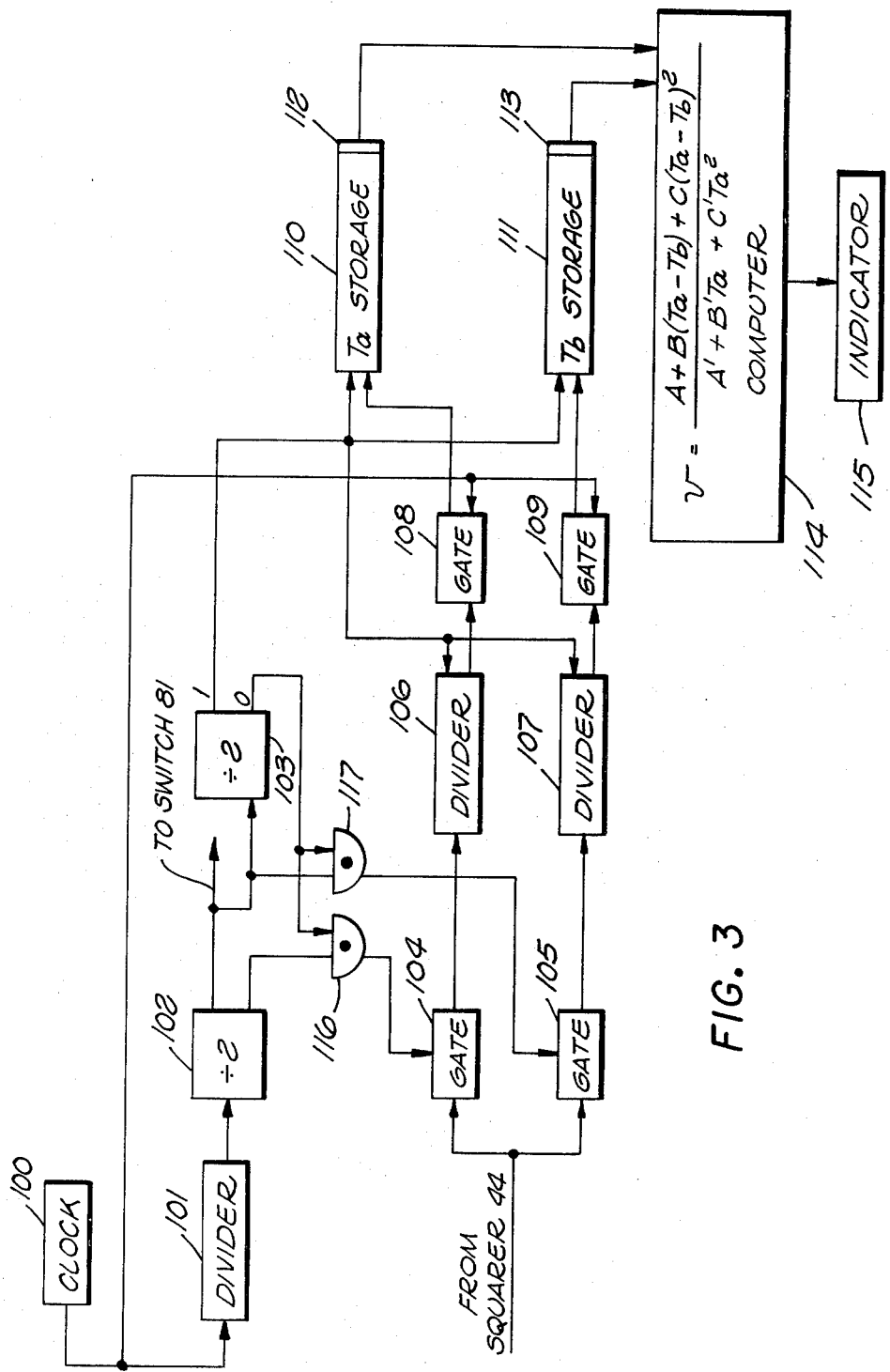
FIG. 3 is a diagrammatic view of a function generator shown in FIG. 1.

In FIG. 3, a clock 100 operating through a divider 101, and dividers 102 and 103 open gates 104 and 105, and operate switch 81' (FIG. 2) alternately in synchronism therewith.

Dividers 106 and 107 and gates 108 and 109 in FIG. 3 cause counters 110 and 111 to count the clock for periods $T_a$ and $T_b$, respectively, where $T_a$ is the period of the signal on lead 33 when it lags that on lead 32. The period $T_b$ is the period of the signal on lead 33 when it leads that on lead 32.

Digital-to-analog converters are provided at 112 and 113 although these may be omitted when a digital computer is employed rather than an analog computer as at 114. If desired, an indicator 115 may be connected from computer 114 and act as utilization means 31. $T_a$ storage 110 and $T_b$ storage 11 may be updated counters reset by the "1" output of divider 103. Gates 108 and 109 admit clock pulses to counters 110 and 111 alternately. Dividers 106 and 107 provide varying pulse widths to gates 108 and 109, respectively, somewhat less than those of the output of divider 101. Dividers 106 and 107 are also reset by the "1" divider output of divider 103.

Gates 104, 116, 105 and 117 alternately gate pulses from squarer 44 (FIG. 2) to dividers 106 and 107.

Figure 4:
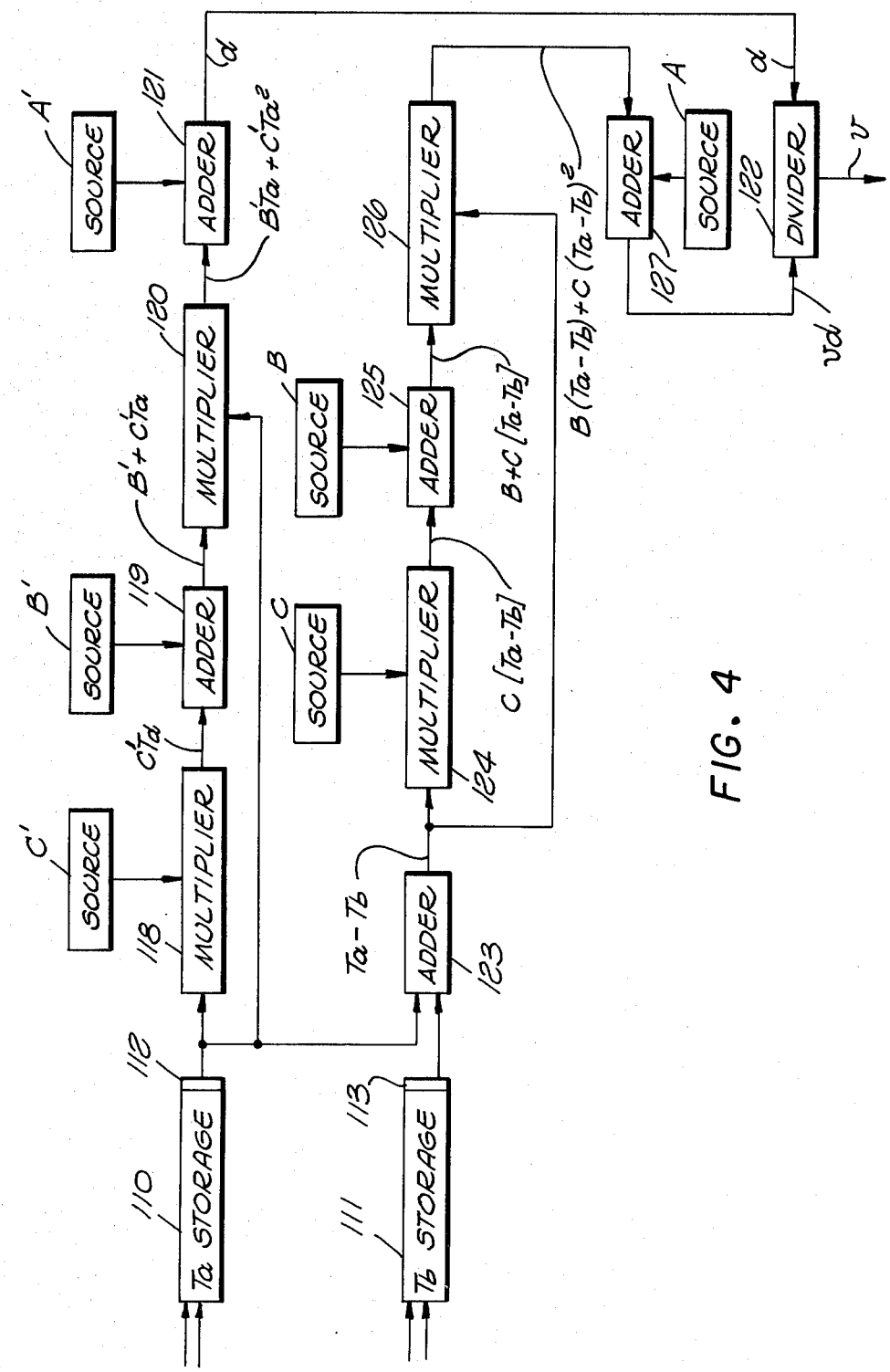
FIG. 4 is a diagrammatic view of a computer shown in FIG. 3.

Computer 114 is shown in greater detail in FIG. 4. A multiplier 118, and adder 119, a multiplier 120, and an adder 121 are connected in succession from converter 112 to a divider 122. An adder 123, a multiplier 124, an adder 125, a multiplier 126, and an adder 127 are connected from converter 113 to divider 122.

Sources C, B, A, C', B' and A' are respectfully connected to multiplier 118, adder 119, adder 121, multiplier 124, adder 125, and adder 127.

In accordance with present invention, it has been found that the output of divider 122 will be directly proportional to dynamic or kinematic viscosity v of the fluid in which the wire loop 24 is immersed and where $$vd = A + B(T_a - T_b) + C(T_a - T_b)^2 \quad (1)$$

$$d = A' + B'T_a^2 + C'T_a^2 \quad (2)$$

d is the density of the fluid in which wire loop 24 is immersed, and

A, B, C, A', B', and C' are constants which may be obtained empirically from a fluid known viscosity and density. Thus, $$v = \frac{A + B(T_a - T_b) + C(T_a - T_b)^2}{A' + B'T_a + C'T_a^2} \quad (3)$$

Figure 5:
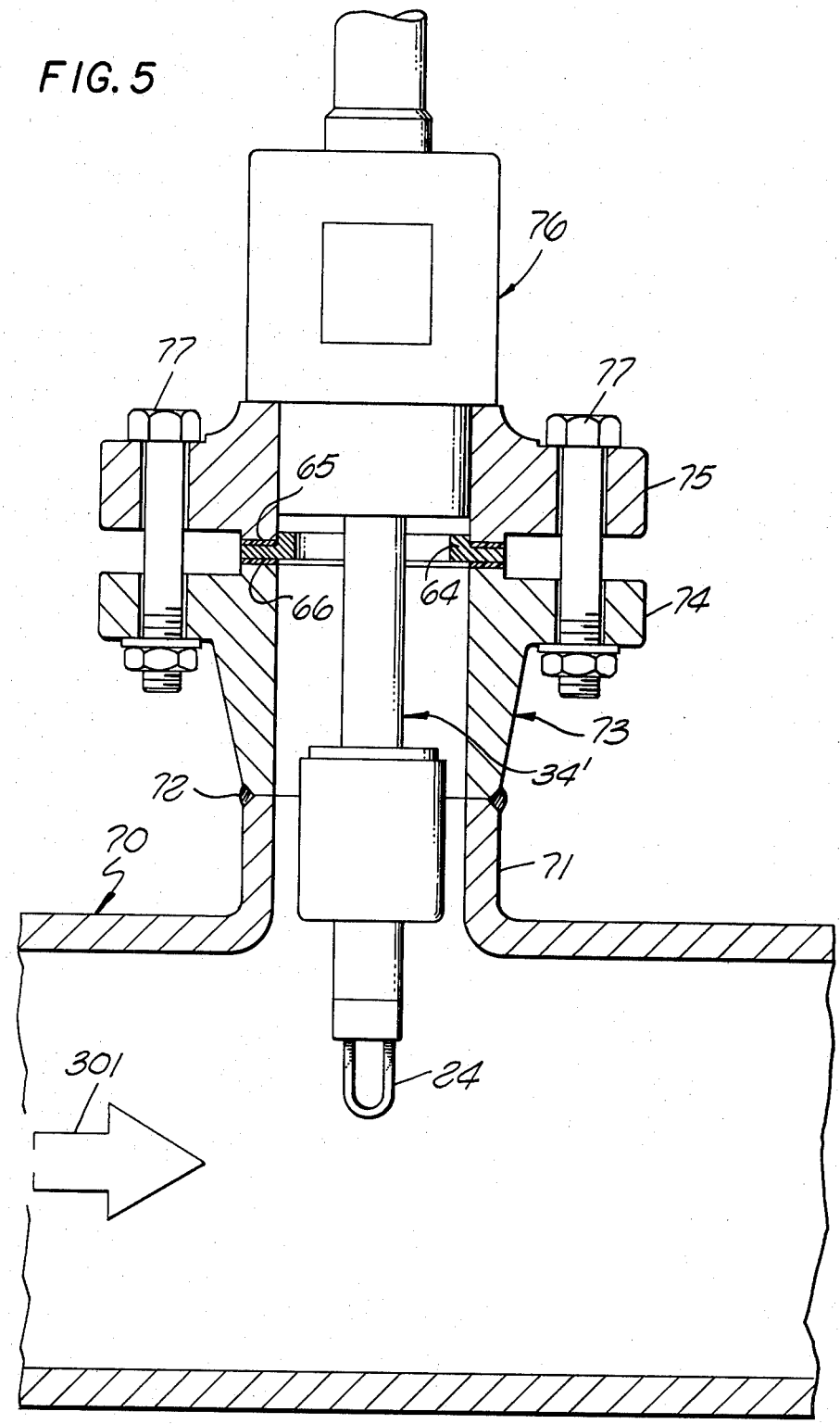
FIG. 5 is a diagrammatic view of a probe shown in FIG. 1.

One embodiment of the probe 34' of the present invention is illustrated in FIG. 5. Gaskets 65 and 66 are bonded onto opposite sides of a ring 64.

Fluid flow is in the direction of an arrow 301.

A pipeline is illustrated at 70 having a hollow cylindrical projection 71 which is welded at 72 to a fitting 73 that has a flange 74 bolted to a flange 75 of an assembly 76 at preferably three or more or, for example, eight places 77.

Figure 6:
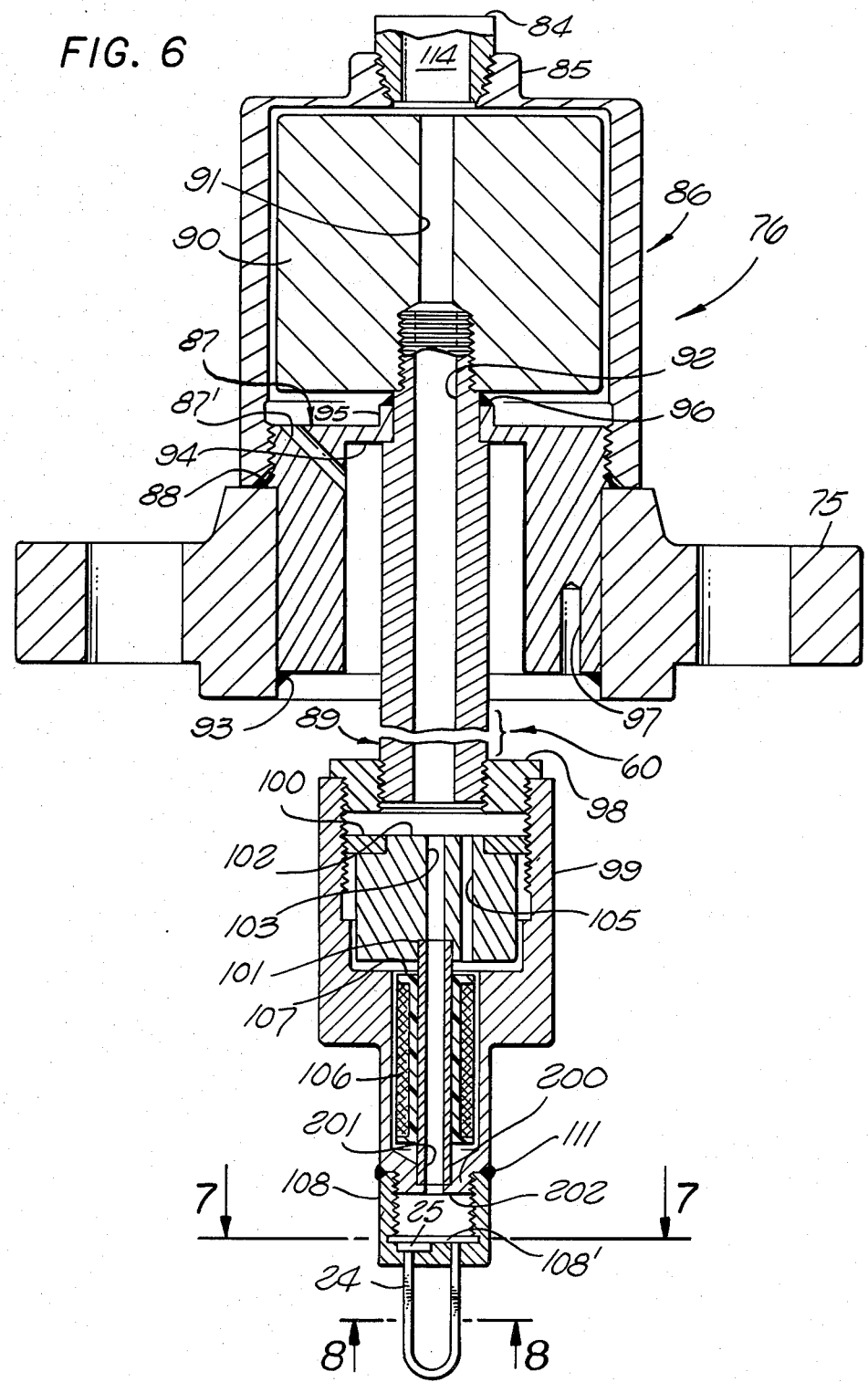
FIG. 6 is a vertical sectional view of the probe shown in FIG. 5.

A vertical section view of probe 34' is shown in FIG. 6 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 and may be welded thereto, if desired. Cylinder 90 is solid except for a hole 91 which extends completely therethrough and is in communication with the hollow interior 92 of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pinhole 97, if desired, so that it may be held while end cap 86 is turned or threaded thereto.

Shaft 89 is, in turn, fixed to a ferrule 98 by being threaded thereinto.

A magnetostrictive tube 101 which is hollow and open at both ends is press fit into a body 102 and press fit into the lower end 200 of a body 99. Body 102 is similar to a body disclosed in the U.S. Pat. No. 3,741,000, issued June 26, 1973, and may be identical thereto, if desired. Alternatively, body 102 may have one hole 103 to receive lead wires from a piezoelectric crystal 25, and a hole 105 to receive lead wires from a drive coil 23 wound on a dielectric spool 107 press fit onto tube 101. Tube 101 extends, at the bottom thereof, through a circular hole 201 in the end 200 of body 99. Bore 201 has a shoulder 202 that the lower end of tube 101 abuts.

A weld at 111 between body 99 and a ferrule 108 is fluid tight.

The upper ends of wire loop 24 are fixed through ferrule 108 in a fluid tight manner.

In FIG. 6, annular portion 108' of ferrule 108 is a relieved portion.

As shown in FIGS. 7 and 8, ferrule 108 has openings for legs 24' and 24" of wire loop 24 to accomodate the rectangular cross sections of the legs 24' and 24".

In the operation of the embodiment of the invention shown in FIG. 6, alternate axial expansion and contraction of tube 101 in compression between shoulder 202 and body 102, causes ferrule 108, body 99 and wire loop 24 to vibrate. Crystal 25 then produces an alternating electrical output signal in synchronism with the wire loop vibration. Crystal 25 must overlie at least a portion of leg 24" or leg 24' (FIG. 7). The crystal output through preamp 26 is supplied over lead 32 in FIG. 2.

Wire loop 24 may have a square, round or other cross section if desired.

What is claimed is:

1. A viscosimeter comprising: a probe having an input lead and an output lead; a loop circuit having an input lead connected from said probe output lead, a first output lead connected to said probe input lead, and a second output lead, said probe and said loop circuit forming an electromechanical oscillator, said probe including a vibratable structure immersable in a fluid, means connected from said probe input lead to vibrate said vibratable structure, a transducer, means connecting said transducer to said first and second output leads, said last named connection producing first and second varying signals on said first and second output leads, respectively both of the same frequency as that at which said vibratable structure vibrates, said first signal having periods $T_a$ and $T_b$ at different times, the product of the kinematic viscosity and density of said fluid being a function of said periods $T_a$ and $T_b$; utilization means; output means connecting said loop circuit second output lead to said utilization means; and phase adjustment means connected to said loop circuit for periodically switching the phase of one of said first and second signals so that said one signal phase altnerates between two different values relative to the phase of the other signal, said one signal being connected from one of said first and second output leads wherein means are connected from said one output lead to provide a signal proportional to the viscosity v of said fluid thus:

$$v = \frac{A + B(T_a - T_b) + C(T_a - T_b)^2}{A' + B'T_a + C'T_a^2}$$

where $T_a$ is the period during which said one signal lags,
$T_b$ is the period during which said one signal leads,
and A, B, C, A', B' and C' are constants such that $A'+B'T_a+C'T_a^2$ is directly proportional to the density of said fluid.

2. The invention as defined in claim 1, wherein said one signal leads and lags the other signal by the same number of electrical degrees.

3. The invention as defined in claim 2, wherein said one signal alternately leads and lags the other signal each time by 30 electrical degrees.

4. The invention as defined in claim 1, wherein said vibratable structure includes a resilient loop of wire mounted with its ends substantially fixed in position.

* * * * *